United States Patent [19]

Musso et al.

[11] Patent Number: 5,130,446

[45] Date of Patent: Jul. 14, 1992

[54] FLUORESCENT COMPOUNDS FOR TAGGING NUCLEIC ACID PROBES

[75] Inventors: Gary F. Musso; Soumitra Ghosh, both of San Diego; Leslie E. Orgel, La Jolla; Geoffrey M. Wahl, San Diego, all of Calif.; Emil T. Kaiser, New York, N.Y.

[73] Assignee: Siska Diagnostics, Inc., La Jolla, Calif.

[21] Appl. No.: 323,433

[22] Filed: Mar. 14, 1989

Related U.S. Application Data

[62] Division of Ser. No. 122,496, Nov. 16, 1987, Pat. No. 4,833,251, which is a division of Ser. No. 748,499, Jun. 25, 1985.

[51] Int. Cl.$^5$ ............................................. C07D 311/82
[52] U.S. Cl. .................................... 549/223; 549/227; 435/6
[58] Field of Search ............... 549/344, 370, 394, 223, 549/227

[56] References Cited

U.S. PATENT DOCUMENTS

| | | | |
|---|---|---|---|
| 4,316,950 | 2/1982 | Cincotta et al. | 430/221 |
| 4,433,051 | 2/1984 | Gilad et al. | 435/7 |
| 4,585,862 | 4/1986 | Wang et al. | 544/319 |
| 4,912,208 | 3/1990 | Fiechtner et al. | 536/53 |

OTHER PUBLICATIONS

J. G. J. Bauman, et al., "Cytochemical Hybridization and Fluorochrome-labeled RNA II", J. Histochem. Cytochem. 29, pp. 238-246 (1981).

D. E. Draper, "Attachment of Reporter Groups to Specific, Selected Cytidine Residues in RNA Using a Bisulfite-catalyzed Transamination Reaction," Nucl. Acids Res. 12, 989-1002 (1984).

D. E. Draper and L. Gold, "A Method for Linking Fluorescent Labels to Polynucleotides: Application to Studies of Ribosome-Ribonucleic Acid Interactions," Biochemistry 19, 1774-1781 (1980).

J. G. J. Bauman et al., "Cytochemical Hybridization with Fluorochrome-labeled RNA I," J. Histochem. Cytochem. 29, 227-237 (1981).

J. G. J. Bauman et al., "A New Method for Fluorescence Microscopical Localization of Specific DNA Sequencers by in situ Hybridization of Fluorochrome-labelled RNA," Exp. Cell. Res. 128, 485-490 (1980).

C. S. Chadwick, et al., "Fluorescent Protein Tracers-A Trial of New Fluorochromes and the Development of an Alternative to Fluorescein," Immunology 1, 315-327 (1958).

J. G. J. Bauman et al., "Cytochemical Hybridization with Fluorochrome-labeled RNA II," J. Histochem. Cytochem. 29, 227-237 (1981).

Primary Examiner—C. Warren Ivy
Assistant Examiner—Barbara Twardzik
Attorney, Agent, or Firm—Fitch, Even, Tabin & Flannery

[57] ABSTRACT

Fluorescent linker moieties are provided which comprise a fluorescent compound such as fluorescein attached to a linker moiety such that a functional group of the linker is available for attachment to an affinity molecule such as a nucleic acid which has an $N^4$ (substituted amino) cytosine moiety. Probes tagged with fluorescent derivatives such as fluorescein, tetramethyrhodamine or tetraethylrhodamine may be detected by fluorescence spectroscopic methods.

3 Claims, No Drawings

FLUORESCENT COMPOUNDS FOR TAGGING NUCLEIC ACID PROBES

This application is a division of application Ser. No. 07/122,496, filed Nov. 16, 1987, now U.S. Pat. No. 4,833,251, which is a division of application Ser. No. 06/748,499, filed Jun. 25, 1985, now abandoned.

TECHNICAL FIELD

The present invention relates to nucleic acid hybridization probes and, more particularly, to the chemical labeling of nucleic acids to make them useful as hybridization probes.

BACKGROUND OF THE INVENTION

The use of single-stranded DNA or RNA probes, to test for the presence of particular DNAs or RNAs and associated biological entities in samples of biological material, is well known. See, e.g., Grunstein and Hogness, Proc. Nat'l. Acad. Sci. (US) 72, 3961–3965 (1975); Southern, J. Mol. Biol. 98, 503–505 (1975); Langer et al., Proc. Nat'l. Acad. Sci. (US) 78, 6633–6637 (1981); Falkow and Moseley, U.S. Pat. No. 4,358,535; Ward, et al., European Patent Application Publication No. 0 063 879; Englehardt, et al., European Patent Application Publication No. 0 097 373; Meinkoth and Wahl, Anal. Biochem. 138, 267–284(1984).

Among areas in which such probes find application are testing of food and blood for contamination by pathogenic bacteria and viruses; diagnosis of fungal, bacterial and viral diseases by analysis of feces, blood or other body fluids; diagnosis of genetic disorders, and certain diseases such as cancers associated with a genetic abnormality in a population of cells, by analysis of cells for the absence of a gene or the presence of a defective gene; and karyotyping. See Klausner and Wilson, Biotechnology 1, 471–478 (1983); Englehardt, et al. supra; Ward et al., supra; Falkow and Moseley, supra.

The principle which underlies the use of such probes is that a particular probe, under sufficiently stringent conditions, will, via hydrogen-bonding between complementary base moieties, selectively hybridize to (single-stranded) DNA or RNA which includes a sequence of nucleotides ("target sequence") that is complementary to a nucleotide sequence of the probe ("probing sequence" specific for the target sequence). Thus, if a biological entity (e.g., virus, microorganism, normal chromosome, mammalian chromosome bearing a defective gene) to be tested for has at least one DNA or RNA sequence uniquely associated with it in samples to be tested, the entity can be tested for using a nucleic acid probe.

A DNA or RNA associated with an entity to be tested for and including a target sequence to which a nucleic acid probe hybridizes selectively in a hybridization assay is called "target" DNA or RNA, respectively, of the probe.

A probe typically will have at least 8, and usually at least 12, ribonucleotides or 2′-deoxyribonucleotides in the probing sequence that is complementary to a target sequence in its target DNA or RNA. Outside the probing sequences through which a probe complexes with its target nucleic acid, the probe may have virtually any number and type of bases, as long as the sequences including these additional bases do not cause significant hybridization with nucleic acid other than target nucleic acid under hybridization assay conditions. That is, a probe will be specific for its target DNA or RNA in hybridization assays.

To be useful in analyzing biological samples for the presence of a target DNA or RNA, a polynucleotide probe must include a feature which will render detectable the duplex formed when the probe is hybridized to its complementary sequence in the target (single-stranded) DNA or RNA. Typically, such features in a probe include radioactive atoms or pyrimidine or purine bases chemically modified to include moieties which are readily and sensitively detected by any of a number of techniques.

For example, a probe may be made with $^{32}$P-labelled nucleoside triphosphates; then the probe itself, as well as target DNA or RNA with the probe hybridized to it, can be detected by means of radiation from $^{32}$P-decay. Probes whose detectability is based on radioactive decay are unsuitable for many applications because of safety problems and licensing requirements associated with radioactive materials and because of degradation of the probes that occurs with radioactive decay during storage. Thus, probes whose detectability is based on chemical modification of pyrimidine or purine bases are preferred in many situations.

There are numerous examples of modified purine or pyrimidine bases in probes wherein a moiety, herein referred to as a "tag moiety," is chemically linked to render detectable target DNA or RNA hybridized with probe. See, e.g. Ward et al., supra; Englehardt et al., supra; Klausner and Wilson, supra. Typically, the "tag moiety" is a moiety to which a protein will bind with high affinity, e.g. an antigen to which an antibody binds; a biotinyl or iminobiotinyl moiety to which avidin or streptavidin will bind; an inhibitor of an enzyme to which the enzyme binds. A protein which binds with high affinity to a tag moiety of a probe is referred to herein as a "conjugate protein" of the tag moiety.

In a typical assay, after probe is hybridized to target DNA or RNA, a "reporter group" is added to the system and binds to the tag moiety or moieties of the hybridized probe. A "reporter group" provides a signal which renders detectable the probe that is hybridized to target DNA or RNA. A typical reporter group is a conjugate protein of the tag moiety or a complex, involving such a conjugate protein, which binds to tag through the binding site for tag in the conjugate protein. The reporter group so bound is then detected by an appropriate immunological, physical, or biochemical technique. For example, if the reporter group is simply a conjugate protein, detection might be by any of a number of well known immunoassay techniques, based on antibodies directed against the conjugate protein. If the reporter group is a conjugate protein which naturally contains a chromophore or fluorophore, or is a conjugate protein modified to include such a moiety, detection might be by a spectroscopic technique based on the chromophore or fluorophore. If the reporter group is a heteropolymer or homopolymer of enzymes, including a conjugate protein, detection could involve detection of substances produced by enzymatic reactions catalyzed by enzymes in the polymer. Ward et al., supra, Englehardt, et al., supra, and Klausner and Wilson, supra, describe a number of techniques for assaying reporter groups bound to tag moieties of probes.

A tag moiety itself, without being bound by a reporter group, might provide detectability to a probe. For example, a tag moiety which is a fluorophore or chromophore can be detected with a suitable spectroscopic technique without binding of a reporter group. See, e.g., Bauman et al., J. Histochem. Cytochem. 29, 227-237(1981).

In some cases wherein pyrimidine or purine bases are chemically modified by the addition of a tag moiety, a linking moiety will separate the tag moiety from the site of modification on the pyrimidine or purine base. See, e.g., the Ward et al. and Englehardt et al. references, supra. In some cases, such linking moieties facilitate the attachment of tag moieties to probe. Further, a linking moiety tends to hold a tag moiety some distance from the modified purine or pyrimidine base, thereby increasing accessibility of the tag moiety to binding by a reporter group and, further, reducing interference with formation or stability of duplexes between probe and target DNA or RNA in those instances where the tag moiety has a large molecular weight.

Polynucleotide probes which comprise at least one cytosine moiety modified to have a tag moiety linked, directly or through a linking moiety, to the $N^4$-position, have not been available heretofore.

Because the amino group at the 4-position of cytosine is involved in hydrogen-bonding between cytosine and guanine moieties in nucleic acid duplexes, it has been thought heretofore that modifications to this amino group would be unacceptable in nucleic acid probes. It has been thought that such modifications in a nucleic acid would interfere with duplex formation, and thereby result in a probe with unacceptable specificity and sensitivity, by severely disrupting guanosine-cytosine hydrogen-bonding. See Ward et al., supra; Ruth, Patent Cooperation Treaty International Publication No. WO84/03285(1984).

The chemistry of modifying cytosine moieties at the $N^4$-nitrogen has been studied with cytidine and 2'-deoxycytidine and their phosphates, both as monomers and included in single-stranded polynucleotides. Nitta et al., FEBS Letters 166, 194-198 (1984); Negishi et al. (I), Nucl. Acids Res. Symp. Series 12, pp. 29-30(1983); Negishi et al., (II), Nucl. Acids Res. 11, 5223-5333 (1983); Hayatsu, Prog. Nucleic Acid Res. and Mol. Biol 16, 75-124 (1976).

The $N^4$-amino group, in $N^4$-aminocytidine and $N^4$-amino-2'-deoxycytidine and their phosphates, both as monomers and included in single-stranded polynucleotides, is known to have reactivities characteristic of substituted hydrazines and reacts accordingly with aldehydes, ketones, isothiocyanates and imidates. Nitta et al., supra; Negishi (I), supra; Hayatsu, supra. See also P. Smith, The Chemistry of Open-Chain Organic Nitrogen Compounds, W. A. Benjamin Inc., New York, New York, Vol. II, pp. 119-209 (1966).

Nitta et al., supra, have reported transamination of cytosine moieties in polycytidine with hydrazine in the presence of bisulfite; and derivatization of the transaminated product with an adduct of glutathione with pyruvic acid, wherein the adduct reacts through the keto-carbon of pyruvate with the $N^4$-amino group.

SUMMARY OF THE INVENTION

We have discovered nucleic acid probes which comprise a cytosine moiety modified to $N^4$-(substituted amino)cytosine, wherein the substituent on the amino group comprises a tag moiety.

We have discovered, further, polynucleotides, with cytosines modified to $N^4$-amino cytosines, which are intermediates in the syntheses of the polynucleotide probes of the present invention. We have also discovered novel compounds, which can be used to link certain tag moieties to polynucleotides comprising $N^4$-aminocytosine moieties to make polynucleotide probes according to the invention, and novel methods to make probes of the invention which comprise reacting the novel compounds with polynucleotides comprising $N^4$-aminocytosine moieties.

Duplexes between the probes of the invention and target DNA and RNA to which they bind are also part of our discovery, as are the duplexes complexed with reporter groups.

In yet another aspect of the invention, we have discovered a novel method for testing a sample for the presence of a biological entity, associated with a target DNA or RNA. Such method comprises combining single-stranded DNA or RNA, derived from the sample, with a nucleic acid probe of the invention specific for the target DNA or RNA. Reaction conditions for carrying out the method are selected whereby stable duplexes form between probe and at least a portion of its target nucleic acid but significant duplex formation between probe and non-target nucleic acids present in the sample is excluded. The method also comprises detecting said stable duplexes by means of a signal from the tag moiety directly or from a reporter group, which is bound to the tag moiety.

Finally, our invention encompasses kits for testing samples for the presence of a biological entity associated with target DNA or RNA, which will be present in a sample only if the biological entity is present. Such kits comprise a polynucleotide which has a sequence complementary to a sequence within the target DNA or RNA but not other DNA or RNA in samples to be tested. In one embodiment, the kits include, in addition to the polynucleotide, reagent to convert cytosine moieties in the polynucleotide to $N^4$-aminocytosines. In a further embodiment, the kits comprise a probe according to the invention, with cytosines of the polynucleotide modified to $N^4$-(substituted amino)cytosines wherein the substituent on the amino group includes a tag moiety.

DETAILED DESCRIPTION OF THE INVENTION

In one aspect, the present invention is a nucleic acid probe which comprises a modified cytosine moiety of Formula I

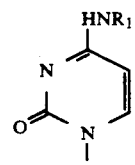

wherein $R_1$ is (i) $-N=C(R_2)-R_5-R_6$, (ii) $-NH-(CHR_2)-R_5-R_6$, or (iii) $-NH(C=R_3)NH-R_5-R_6$.

wherein $R_2$ is hydrogen or alkyl of 1 to 4 carbon atoms; $R_3$ is sulfur or oxygen; $R_5$ is a linker moiety; and $R_6$ is a tag moiety.

The nitrogen atom, at the terminus of the $R_1$ groups of Formula I that is bonded to the $N^4$-position of cytosine, is the nitrogen atom of the group referred to herein as the $N^4$-amino group of $N^4$-aminocytosine moieties.

In another aspect, the invention includes duplexes formed between such a probe and its target DNA or RNA in a sample tested with the probe. The invention includes, further, such duplexes complexed with a reporter group conjugate to the tag moiety on the probe.

In yet another aspect, the invention relates to a method for testing a sample for a target DNA or RNA which comprises (i) combining, with the target DNA or RNA, a nucleic acid probe specific for the target DNA or RNA, said probe comprising a modified cytosine moiety of Formula I

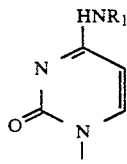

I wherein $R_1$ is (i) $-N=C(R_2)-R_5-R_6$, (ii) $-NH-(CHR_2)-R_5-R_6$, or (iii) $-NH(C=R_3)NH-R_5-R_6$.

wherein $R_2$ is hydrogen or alkyl of 1 to 4 carbon atoms; $R_3$ is sulfur or oxygen; $R_5$ is a linker moiety; and $R_6$ is a tag moiety; provided that the derivation of single-stranded nucleic acid from said sample and the combining of said single-stranded nucleic acid with said probe are under conditions whereby stable duplexes form between the probe and at least a portion of the target nucleic acid but not significantly between the probe and non-target DNA or RNA; and (ii) determining whether stable duplex was formed in step (i) by (a) separating unduplexed probe from duplexed probe formed in step (i); (b) if the tag moiety, $R_6$, provides detectability through binding thereto of a reporter group, combining the duplexed probe with a reporter group conjugate to said tag moiety, under conditions whereby the reporter group binds to at least a portion of any of said tag moiety that is present, and then separating from the product so treated substantially all reporter group not bound to said tag moiety; (c) treating the product of step (i), after treatment according to step (ii)(a) and, if used, step (ii)(b), to produce a signal from any of said tag that is present, if tag without bound reporter group provides a signal to render probe detectable, or from any of said bound reporter group that is present; and (d) determining whether a detectable signal is generated by the treatment of step (ii)(c). The treatment of step (ii)(c) will depend on the tag moiety or reporter group which is to provide the signal and on the type of signal to be provided. If, for example, the signal is to be fluorescence emission, the treatment can be simply exposure to electromagnetic radiation of wavelength suitable to stimulate the emission from the tag moiety or reporter group. To cite another example, if the signal is to be the appearance of a visible color due to a reaction catalyzed by an enzyme which is part of a reporter group, the treatment will involve combination of the product of step (i), after treatment according to steps (ii)(a) and (ii)(b), with substrates for the enzyme and any other compounds necessary to produce the substance which provides the color. The determination of step (ii)(d), of whether a detectable signal is generated, will involve observation, with the naked eye or with suitable instrumentation if necessary, to detect any signal that might be generated. Also, usually the method will be carried out in parallel on the sample being tested (test sample), a sample of nucleic acid known to be free of DNA or RNA with target segment of the probe (negative control), and possibly also a sample known to contain DNA or RNA with target segment of the probe (positive control). When the method is so carried out, in parallel on test sample, negative control and positive control, the determination will then involve comparing the signals from the samples to ascertain that the assay system was functional (producing a signal from the positive control that is greater than "background" signal, from the negative control) and whether the signal detected from the test sample was greater than "background" signal. When signal from test sample is determined to be greater than background signal, the test sample signal can be ascribed to target DNA or RNA in the test sample.

The invention entails also a number of kits for testing samples for the presence of a biological entity that is associated with a target DNA or RNA which is present in the sample only if the biological entity is present. One of said kits comprises (i) a quantity of a nucleic acid which comprises a cytosine moiety and has a sequence of a probe specific for said target DNA or RNA and (ii) reagents to convert at least a portion of the cytosine moieties in said quantity of nucleic acid to $N^4$-aminocytosine moieties. Another of said kits comprises a nucleic acid, which comprises an $N^4$-aminocytosine moiety and has a sequence of a probe specific for said target DNA or RNA. Yet another of the kits according to the invention comprises a nucleic acid probe specific for said target DNA or RNA, which probe comprises a modified cytosine moiety of Formula I

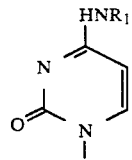

I wherein $R_1$ is (i) $-N=C(R_2)-R_5-R_6$, (ii) $-NH-(CHR_2)-R_5-R_6$, or (iii) $-NH(C=R_3)NH-R_5-R_6$, wherein $R_2$ is hydrogen or alkyl of 1 to 4 carbon atoms; $R_3$ is sulfur or oxygen; $R_5$ is a linker moiety; and $R_6$ is a tag moiety.

The invention entails further a compound of Formula LII

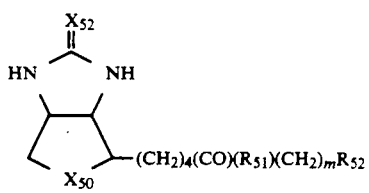

LII wherein —$R_{51}$— is —NH— or —NH—N=C($R_{511}$)—, wherein the amino group is bonded to the carbonyl group and wherein $R_{511}$ is hydrogen or alkyl of 1 to 4 carbon atoms; wherein $R_{52}$ is —$CO_2R_{53}$, —(CO)$R_{54}$,

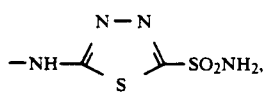

wherein $R_{53}$ is alkyl of 1–5 carbon atoms; wherein $R_{54}$ is hydrogen, alkyl of 1–5 carbon atoms or chloro; wherein $R_{55}$, $R_{56}$ and $R_{57}$ are the same or different and are each alkyl of 1–6 carbon atoms; wherein $R_{58}$ and $R_{59}$ are the same or different and are each alkyl of 1–5 carbon atoms; wherein $R_{60}$ is alkylene of 2 or 3 carbon atoms; wherein m is 2 to 20; wherein $X_{50}$ is S or S=O; and wherein $X_{52}$ is O or NH.

The invention includes also a compound of Formula XXXII $R_{32}(CO)(CH_2)_kR_{33}$ wherein $R_{32}$ is

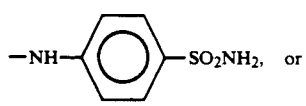

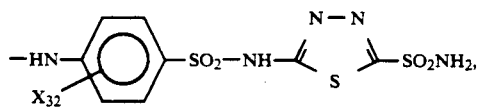

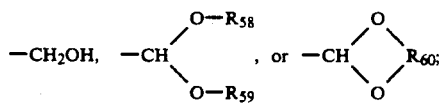

wherein $X_{32}$ is hydrogen, halogen or —$NO_2$; wherein $R_{33}$ is —CHO, —$CO_2H$, —$CH_2OH$, 

wherein $R_{58}$ wherein $R_{58}$ and $R_{59}$ are the same or different and are each alkyl of 1–5 carbon atoms; wherein $R_{60}$ is alkylene of 2 or 3 carbon atoms; and wherein k is 2 to 20.

"Halogen" means fluoro, chloro, bromo or iodo.

Another compound of the invention is of Formula XLV:

$R_{45}(NH)(C=R_{46})(NH)(CH_2)_jR_{47}$ wherein $R_{45}$ is fluorescein, tetramethylrhodamine, or tetraethylrhodamine; $R_{46}$ is oxygen or sulfur; $R_{47}$ is —CHO, —$CO_2H$, —$CH_2OH$,

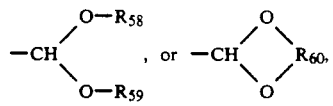

wherein $R_{58}$ and $R_{59}$ are the same or different and are each alkyl of 1–5 carbon atoms; where $R_{60}$ is alkylene of 2 or 3 carbon atoms; and wherein j is 2 to 20.

Preferably in the compound of formula XLV, $R_{47}$ can be $R_{48}$ wherein $R_{48}$ is —CHO or

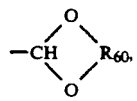

wherein $R_{60}$ is alkylene of 2 or 3 carbon atoms.

Compounds of Formulas LII, XXXII, and XLV are intermediates in preparations of preferred probes of the invention.

The present invention also entails processes for making compounds of Formulas LII, XXXII, and XLV. These processes are taught in examples below.

The invention entails further a process for making a preferred nucleic acid probe of the invention, which comprises a modified cytosine moiety of Formula LIX

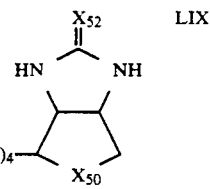 LIX

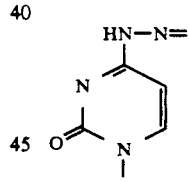

wherein $X_{50}$ is S or S=O; wherein $X_{52}$ is O or NH, wherein —$R_{51}$— is —NH— or —NH—N=C($R_{511}$)—, wherein the amino group is bonded to the carbonyl group and wherein $R_{511}$ is hydrogen or alkyl of 1 to 4 carbon atoms; and wherein m is 2 to 20, which process comprises reacting a nucleic acid, with the same sequence as the probe and comprising an $N^4$-aminocytosine moiety, with a compound of Formula LX

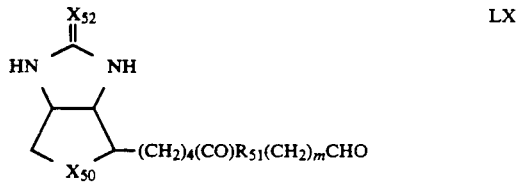 LX wherein $X_{50}$, $X_{52}$, $R_{51}$ and m are as in the compound of Formula LIX. More preferred values for m are 5 to 8. When $X_{50}$ is S=O, $X_{52}$ is preferably O. Most preferably $X_{50}$ is S and $X_{52}$ is 0. Preferably $R_{511}$ is hydrogen; more preferably $R_{51}$ is —NH—.

The invention still further involves a process for making another preferred nucleic acid probe of the invention, which comprises a modified cytosine moiety for Formula LVII

LVII

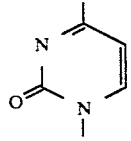

wherein $R_{32}$ is

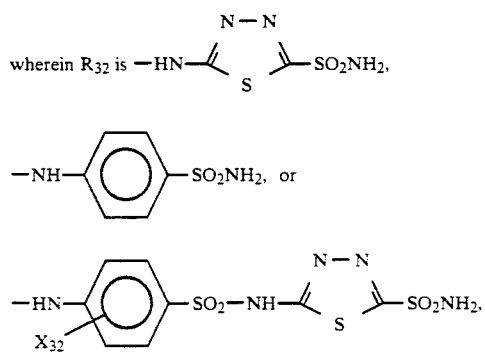

wherein $X_{32}$ is hydrogen, halogen or —$NO_2$; and wherein k is 2 to 20, which process comprises reacting a quantity of the nucleic acid with the same sequence as the probe and comprising an $N^4$-aminocytosine moiety with a compound of the Formula XXXIV $R_{32}(CO)(CH_2)_kCHO$ wherein $R_{32}$ and k are as in the compound of Formula LVII. More preferred values for k are 5 to 8. Preferably $R_{32}$ is the aminothiadiazole-benzolamide derivative,

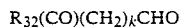

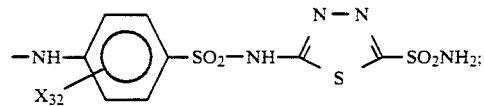

most preferably, among these derivatives, $X_{32}$ is hydrogen. The derivative wherein $X_{32}$ is hydrogen is hereinafter referred to as PABSAT (for p-amino-benzenesulfonamide with aminothiadiazole).

In another embodiment the invention involves a process for making still another preferred nucleic acid probe of the invention, which comprises a modified cytosine moiety of Formula XLVI

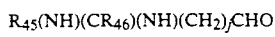

XLVI

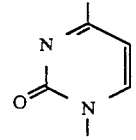

wherein $R_{45}$ is fluorescein, tetramethylrhodamine or tetraethylrhodamine; $R_{46}$ is oxygen or sulfur; and j is 2 to 20, which process comprises reacting a quantity of the nucleic acid with the same sequence as the probe and comprising an $N^4$-aminocytosine moiety with a compound of Formula XLVII.

$R_{45}(NH)(CR_{46})(NH)(CH_2)_jCHO$ wherein $R_{45}$, $R_{46}$, and j are as in the compound of Formula XLVI. More preferred values for j are 5 to 8. Preferably $R_{45}$ is fluorescein or tetramethylrhodamine and $R_{46}$ is sulfur.

A nucleic acid with the same sequence as a probe and comprising an $N^4$-aminocytosine can be provided by reacting a quantity of nucleic acid which has the same sequence as the probe with hydrazine in the presence of bisulfite to convert at least a portion of the cytosine moieties in said quantity of nucleic acid to $N^4$-aminocytosine moieties.

A nucleic acid with the sequence of a probe can be made by any of various in vitro synthesis techniques known in the art followed by purification of the nucleic acid of desired sequence by high performance liquid chromatography (HPLC) or any other standard method known in the art. One of these techniques, involving automated solid-phase, step-wise chemical synthesis, utilizing phosphoramidate chemistry of Matteucci and Caruthers, and Beaucage and Caruthers, and purification of the nucleic acid of desired sequence by HPLC, is described in greater detail in Example I below.

When a nucleic acid with the sequence of the probe is prepared by an in vitro, step-wise chemical synthesis, the sequence of the entire nucleic acid will typically be complementary to the sequence of the particular segment of target DNA or RNA with which the probe is to hybridize in a hybridization assay. This segment of target DNA or RNA is referred to as the target segment corresponding to the probe.

A nucleic acid with the sequence of the probe can also be prepared in vivo. For example, a double-stranded nucleic acid which includes the sequence of the target segment can be isolated (as by restriction endonuclease cleavage from the chromosomal or episomal DNA of the biological entity to be tested for with the probe) or prepared chemically (as by step-wise solid phase synthesis of both strands followed by annealing of the strands after synthesis and purification) and then cloned using standard techniques in a standard cloning vector, such as pBR322. For example, the pBR322 with the target segment insert can be prepared in large quantities using standard preparative techniques for plasmid DNA, which may include growth of transformed E. coli in the presence of chloramphenicol for a number of doubling times to suppress chromosomal and enhance plasmid replication. The pBR322 with target segment insert can be isolated by known techniques. If target nucleic acid is double-stranded DNA or RNA, both strands of said pBR322 are useful as nucleic acid with sequence of probe. If target nucleic acid is single-stranded DNA or RNA, one or the other of the strands of the pBR322 will be nucleic acid with the sequence of the probe. The chemistry described in detail below, for transamination of cytosines and attachment of tag moieties to $N^4$-amino groups of the transaminated cytosines, can be carried out on the pBR322 in single-stranded form to prepare probe of the invention.

Another method for obtaining nucleic acid with the sequence of the probe is to insert a double-stranded segment which includes a target segment into RF-form DNA of a filamentous bacteriophage, such as M13mp8, M13mp9, M13mp18 or M13mp19, as are known in the art and commercially available, transforming a suitable strain of E. coli, such as E. coli JM101 or JM103, also known and commerically available, with the recombinant RF-form DNA, selecting and culturing the transformed E. coli by known techniques, isolating phage from the culture medium, and finally isolating the single-stranded phage DNA from the phage by standard techniques. When a segment is inserted into RF-DNA, half of the resulting phage population will have DNA which includes an insert with a sequence which is complementary to that of the insert in the other half. If target DNA or RNA is double-stranded, both types of phage DNA will be nucleic acid with sequence of probe. If target DNA or RNA is single-stranded, only half of the phage DNA will be nucleic acid with probe sequence. Of course, as the skilled will recognize, the DNA including the target segment can be inserted asymmetrically into RF-DNA so that all of the resulting phage population will have DNA with the same insert and all of the resulting phage DNA will be nucleic acid with sequence of probe. The phage DNA will be treated chemically as described below to transaminate cytosines and link tags to $N^4$-amino groups of the transaminated cytosines to make a probe of the invention.

RNAs with sequences of probes can be prepared by in vitro chemical techniques, by employing suitably protected ribonucleosides in place of 2'-deoxyribonucleosides. RNAs with sequences of probes can also be prepared enzymatically by known techniques using suitable DNA templates.

Cytosines in RNAs can be transaminated and subsequently linked to tag using essentially the same chemistry as described below for DNAs.

Alternatively, rather than first preparing a nucleic acid with a sequence of the probe and then transaminating cytosines in the nucleic acid, the nucleic acid with the same sequence as the probe and comprising an $N^4$-aminocytosine can be made directly by in vitro synthesis, including enzymatic and solid-phase chemical, using suitable analogs of $N^4$-aminocytidine or $N^4$-amino-2'-deoxycytidine.

In still a further aspect, the invention provides processes for making nucleic acid precursors of probes according to the invention by step-wise, solid-phase syntheses using suitably protected analogs of $N^4$-aminocytidine or $N^4$-amino-2'-deoxycytidine. Example III teaches such a process utilizing the phosphoramidate chemistry of Matteucci and Caruthers, and Beaucage and Caruthers. In view of the teaching of Example III, similar processes involving other methods for step-wise chemical synthesis of polynucleotides, in solution or solid-phase, such as triester methods, will be apparent to the skilled.

Finally, the present invention entails novel, protected analogs of $N^4$-aminocytidine and $N^4$-amino-2'-deoxycytidine which are employed in the processes provided by the invention for in vitro, step-wise synthesis of nucleic acid precursors of probes according to the invention. Certain of these analogs are described in Example III; from those described, others will be apparent to the skilled in the art.

As indicated above, the preferred tag moieties of probes of the invention are biotin, iminobiotin, sulfenylbiotin, aminothiadiazole, sulfanilamide, PABSAT, fluorescein and tetramethylrhodamine. Most preferred are biotin and PABSAT. They are preferably linked to the $N^4$-amino group of $N^4$-aminocytosines through a hydrazone linkage and an n-alkyl chain of 2 to 20 carbon atoms, preferably 5 to 8 carbon atoms.

Probes with the hydrazine linkage can be prepared from probes with the hydrazone linkage by simply reducing the probe (with linked tag) after formation of probe with the hydrazone linkage.

Probes wherein the tag is linked to the $N^4$-amino group of $N^4$-amino-cytosines through a linkage of Formula —$(C=R_3)NH$—, wherein $R_3$ is oxygen or sulfur (preferably sulfur), and a linker moiety —$R_5$— (preferably an n-alkylene chain of 2 to 20, more preferably 5 to 8, carbon atoms) are prepared by first making an isocyanate or isothiocyanate-derivatized tag moiety of Formula $R_3=C=N—R_5—R_6$ (wherein $R_6$ is the tag moiety, preferably one of the preferred eight of the invention) and then reacting a quantity of nucleic acid with the same sequence as the probe and comprising an $N^4$-aminocytosine moiety with the compound of Formula $R_3=C=N—R_6$.

Compound of Formula $R_3=C=N—R_5—R_6$ are prepared by methods known in organic chemistry by first preparing the amino-derivatized compound of Formula $H_2N—R_5—R_6$ and then reacting the compound of Formula $H_2N—R_5—R_6$ with thiophosgene or phosgene.

Probes with biotin, iminobiotin or sulfenylbiotin tag are detected by complexing probe (preferably after hybridization to target) with a reporter group, which includes a streptavidin or avidin molecule as conjugate protein to the tag, and then generating a signal from the reporter group. The method of generating a signal depends on which compounds besides streptavidin or avidin are included in the reporter group. Several reporter groups with avidin or streptavidin, for binding to biotin, are known in the art (see Ward et al., supra; Englehardt et al., supra; Klausner and Wilson, et al., supra) and commercially available, as from Enzo Biochemicals, Inc., New York, N.Y., U.S.A., Bethesda Research Laboratories, Inc., Gaithersburg, Md., U.S.A; and Vector Laboratories, Inc., Burlingame, Calif., U.S.A. These groups include acid or alkaline phosphatase complexed with streptavidin or avidin-DH (detection colorimetrically of a product produced enzymatically by the phosphatase), horse radish peroxidase complexed with streptavidin or avidin-DH (detection colorimetrically of a product produced enzymatically by the peroxidase), and streptavidin alone (detection fluorometrically of fluorescein-labeled anti-streptavidin antibody bound to the streptavidin). The preferred system is the avidin-DH-biotinylated alkaline phosphatase polymer system described by Leary et al., Proc. Natl. Acad. Sci. (U.S.A.) 80, 4045-4049(1983).

Avidin-DH is a highly pure grade of avidin available from Vector Laboratories, Inc., Burlingame, Calif., U.S.A. Highly pure avidin from sources other than Vector Laboratories can also be employed in the present invention.

Probes with aminothiadiazole, sulfanilamide or PABSAT as tag are detected with a reporter group which includes carbonic anhydrase as conjugate protein. Preferred reporter group is polymerized carbonic anhydrase B from a mammalian (preferably bovine) erythrocyte, said polymer prepared as described by Epton, Biochem. Soc. Trans. 5, 277-279(1977). The preferred method of detecting bound carbonic anhydrase polymer is by the fluorescein diacetate assay of Leary, Anim. Blood Grps. Biochem. Genet. 9, 65-67(1978). See also Livesey, Anal. Biochem. 77, 552-561(1977).

Other detection systems (e.g., immunological, based on antibody-binding to carbonic anhydrase) may be employed. Further, heteropolymers of carbonic anhydrase with other enzymes can be employed as reporter group for probes of the invention tagged with aminothiadiazole, sulfanilamide, or PABSAT. Such other enzymes include acid and alkaline phosphatase, beta-galactosidase, and horse radish peroxidase, for which detection systems are well known. See, e.g., Voller et al. "Enzyme-linked Immunosorbent Assay," in Manual of Clinical Immunology, N. Rose and H. Friedman, eds., American Society for Microbiology, Washington, D.C., 2nd Fd.(1980). Biotin-labeled carbonic anhydrase can be employed as reporter group, and all of the systems described above for detection of biotin through binding of avidin or streptavidin can be employed to detect the bound carbonic anhydrase.

Probes with fluorescent tag moieties are readily detected directly, without binding of any reporter group, by fluorescence spectroscopy using methods known in the art. See, e.g., Bauman et al., supra; Bauman et al., Exp. Cell Res. 128, 485–490(1980).

A probe of the invention is used in a hybridization assay for its target DNA or RNA (and, thereby, the biological entity associated with said target) using standard, known nucleic acid probe hybridization assay procedures. See Meinkoth and Wahl, supra, and references cited therein.

The assay of a sample will generally be carried out in parallel with an assay of a blank which contains approximately the same amount of nucleic acid as the sample but is known to contain no DNA or RNA with target segment for the probe (negative control) and may also be carried out in parallel with an assay of a sample known to contain target DNA or RNA (positive control).

The assay of test sample (or blank or positive control) typically proceeds as follows:

Typically, the assay will be carried out on a solid support, such as nitrocellulose paper, to which single-stranded nucleic acid binds non-covalently.

Nucleic acid of sample is isolated and affixed to the solid support in single-stranded form. These isolation and fixation procedures are carried out so that substantially all of the target segment corresponding to probe in any target nucleic acid present in the sample remains intact.

The solid support then may be prehybridized to substantially eliminate sites available on the support for the non-specific binding of probe.

Then a solution containing probe, in a 10-fold to $10^{12}$-fold, typically about $10^3$ to $10^6$-fold molar excess relative to target segment, is incubated with the solid support under conditions of stringency and for a time sufficient for stable duplex to form between probe and a substantial fraction (preferrably nearly all) of any of its target segment on the filter but not to any significant extent between probe and segments other than target segments.

Then unduplexed or partly duplexed probe is washed from the system by a series of washes (usually 2 or 3) under stringency conditions and over usually short periods of time (minutes) to ensure that substantially only probe stably duplexed to target segment remains in the system.

Those of skill know how to ascertain readily, for a particular probe and solid support, suitable stringency conditions and time periods for the hybridization and post-hybridization washes that will provide acceptable specificity and sensitivity for the assays in which the probe will be employed. See Meinkoth and Wahl, supra.

After unduplexed probe is washed from the system, if reporter group must be bound to tag moiety to render probe detectable, a solution of reporter group conjugate to the tag moiety on the probe is incubated with the solid support. Generally, a 10-fold to $10^6$-fold, usually $10^2$- to $10^4$-fold, molar excess of reporter group relative to tag moiety, will be present in the solution and the incubation will be carried out over a time sufficient to ensure that substantially all tag in the system is bound by reporter group. Then, unbound reporter group is washed from the system. Again, the skilled know how to determine conditions of incubation and post-incubation washing to ensure that most tag in a system is bound by reporter group and that little or no reporter group not associated with tag remains in a system.

The system is then treated appropriately to generate a signal from tag moiety (if tag moiety not bound by a reporter group renders probe detectable) or reporter group in the system. A determination is then made whether such a signal was generated.

If positive control is employed, signal from it is compared with that from blank to ensure that the assay system was functional. If the system was functional, the signal from positive control will be greater than that from blank.

The signal from test sample is compared with that from blank. If signal from test sample is greater than that from blank, target segment was present in the sample.

The invention is now illustrated in the following examples:

EXAMPLE I

Polynucleotides

The following polydeoxyribonucleotides were synthesized using automated solid-phase phosphoramidate methodology (Matteucci and Caruthers, J. Am. Chem. Soc. 103, 3185(1981) and Beaucage and Caruthers, Tetrahedron Lett. 1981, 1859–1862) on a Model 380A Applied Biosystems DNA Synthesizer (Applied Biosystems, Inc., Foster City, Calif., U.S.A.). The oligonucleotides produced with the synthesizer have a free hydroxyl group at both the 5'-end and the 3'-end. From the mixture of polydeoxyribonucleotides of varying lengths produced in a synthesis on the machine, the desired one, which is the longest, is isolated and purified by high performance liquid choromatography (HPLC), utilizing a linear gradient of acetonitrile in 0.1 M triethyl ammonium acetate (pH 7.0) to elute the polydeoxyribonucleotides, as described by Frank et al., Nucl. Acids Res. 11, 4365–4377(1983) at pp. 4369–4370.

Polynucleotide A:
5'-GAAGGGGTATCTTTGGATAAAAG-3'

Polynucleotide B:
5'-CCACCACCTAGAACTAGGATATC-3'

Polynucleotide C:
5'-CCAGGCCAGCCGGAGGGACCCCGGGAGCCCGGGCG-3'

The sequence of Polynucleotide A is complementary to that of a segment of the alpha-mating factor gene of Saccharomyces cerevisiae. The sequence of Polynucleotide B is complementary to that of a segment of the alcohol oxidase gene of Pichia pastoris. The sequence of Polynucleotide C is complementary to that of a segment of the genome of Epstein-Barr virus.

EXAMPLE II

Preparation and Characterization of N$^4$-Amino-2'-Deoxycytidine

Deoxycytidine was converted to N$^4$-aminodeoxycytidine following the procedure of Negishi et al., (I) and (II) supra. To 1.0 g (4.4 mmoles) of deoxycytidine (Calbiochem-Behring, La Jolla, Calif. U.S.A.) was added 10 ml of 4 M hydrazine, 0.1 M bisulfite, 0.1 M sodium phosphate buffer (to adjust pH to 7.0) and the solution was stirred at 60° C. for 4 hours. Then 90 ml of 95% ethanol was added, and the mixture was allowed to sit at −20° C. overnight. The buffer salts were removed by filtration and the filtrate was reduced to a thick oil under reduced pressure. Absolute ethanol was added to afford 270 mg (25%) of a semi-solid N$^4$-amino-2'-deoxycytidine.

To 10 mg (0.041 mmoles) of N$^4$-amino-deoxycytidine was added 10 mg (0.051 mmoles) of 2,4-dinitrobenzaldehyde in 5 ml of 50% aqueous methanol. After stirring for 15 minutes at 25° C., the orange precipitate which formed was filtered off. The hydrazone was purified by chromatography on silica gel using 10% methanol in chloroform as an eluant. After concentration of the peak fractions under reduced pressure, 12 mg (70%) of N$^4$-amino-deoxycytidine-2,4-dinitrophenylhydrazone was isolated and characterized by NMR spectroscopy. The product was further characterized by UV/VIS spectroscope yielding an extinction coefficient of 18,000 at 375 nm (dimethylsulfoxide (DMSO): water, 1:20).

EXAMPLE III

Polynucleotides with N$^4$-Aminocytosines

Cytosines in polynucleotides are modified by incubation at 37° C. in a mixture of 4 M hydrazine with 1 M sodium bisulfite buffered to pH 7 with 0.1 M sodium phosphate, with polynucleotide dissolved to a concentration such that the concentration of cytosines is between about 1.0 and 100 micromolar. Under these conditions, the cytosines in a single-stranded polynucleotide are converted to N$^4$-aminoctyosines with pseudo first-order kinetics with a $t_{\frac{1}{2}}$ of about 30 minutes. Complete conversion occurs in about 4 hours.

In a typical reaction, 200 micrograms of polynucleotide A were incubated in 0.5 ml of 4 M hydrazine, 1 M sodium bisulfite, at pH 7.0 (sodium phosphate buffer) at 37° C. The kinetics of transamination were measured by two methods. In one, the reaction was stopped after various reaction times by separation of hydrazine and bisulfite from the polynucleotide by gel permeation chromatography and then the amount of N$^4$-aminocytosine was determined by reaction of 1 volume of a polynucleotide solution with 0.1 volumes of a solution of 2,4-dinitrobenzaldehyde (20 mg/ml) in dimethylformamide (DMF) for 30 minutes at 23° C., followed by a second gel permeation chromatography step. The amount of 2, 4-dinitrophenylhydrazone-derivatized polynucleotide formed was measured spectrophotometrically. In the other method, the kinetics were determined by complete digestion of the polynucleotide with snake venom phosphodiesterase and subsequent analysis of the monomers by HPLC. Both methods of analysis yielded the same results. Modification of the polynucleotide was complete within 4 hours, and half complete at approximately 30 minutes.

EXAMPLE IV

Synthesis of Polynucleotides Using Bases with Modified Cytosines Directly

Polynucleotide probes can be synthesized by the solid-phase phosphoramidate method of Example I so as to have 4-aminocytosines at specific locations. In contrast, the procedure of Example III results in a random distribution of modified cytosines in the polynucleotide, governed by the mathematics of the Poisson distribution and nearest-neighbor effects. To synthesize a polynucleotide with N$^4$-aminocytosine in place of cytosine at specific locations, suitably protected N$^4$-aminocytidine or N$^4$-amino-2'-deoxycytidine is used in place of cytidine or 2'-deoxycytidine at the appropriate steps in the automated synthesis.

Cytidine or 2'-deoxycytidine is transformed into the corresponding N$^4$-amino analog by incuoation in a solution of 4 M hydrazine and 0.1 M sodium bisulfite for 4 hours at 60° C., following the procedure of Example II (see also Negishi et al. (II), supra). The N$^4$-amino analog is isolated and purified as described by Negishi et al. (II), supra.

The N$^4$-amino-modified nucleosides are then protected for use in automated synthesis in the same manner as other nucleosides. In particular, the N$^4$-amino group, and the 3' and 5' hydroxyls, are perbenzoylated with benzoyl chloride. The 3' and 5' hydroxyls are then liberated by selective hydrolysis. The 5'-hydroxyl is then tritylated with 4'-dimethoxy tritylchloride, and the 3'-hydroxyl is phosphoramidited with methoxymonochloro-N, N-diisopropylaminophosphate. The resulting N-acyl, 5'-trityl, 3'-phosphoramidite derivative of cytidine or 2'-deoxycytidine is then used in the automated synthesizer in the appropriate steps to synthesize the nucleic acid of desired sequence. Removal of the benzoyl group from the N$^4$-amino groups of the resulting modified polynucleotide proceeds along with deprotection of the other groups upon removal of the polynucleotides from the resin.

EXAMPLE V

Biotin-Linker Aldehydes

In this Example, several methods are provided for synthesizing biotin-linker compounds that can be reacted with polynucleotides, modified to have N$^4$-aminocytosines in place of one or more cytosine moieties, to attach biotin as a tag moiety through the N$^4$-amino group of the modified cytosines and thereby provide a probe of the invention.

In the various methods, iminobiotin analogs can be employed in place of biotin analogs. Further, any of the biotin linker aldehyde compounds made as provided in this Example can be oxidized to sulfenylbiotin by oxidation under mild oxidizing conditions. Both iminobiotion (biotin wherein the oxygen bonded to the ring is replaced with NH) and sulfenylbiotin (biotin wherein the sulfur atom is replaced with a sulfenyl group) bind with high affinity to avidin and streptavidin and thereby provide useful tag moieties for the probes of the invention.

(A) Synthesis of Biotin-Linker Aldehydes through an Alcohol Intermediate

This process is illustrated in SCHEME I.

SCHEME I

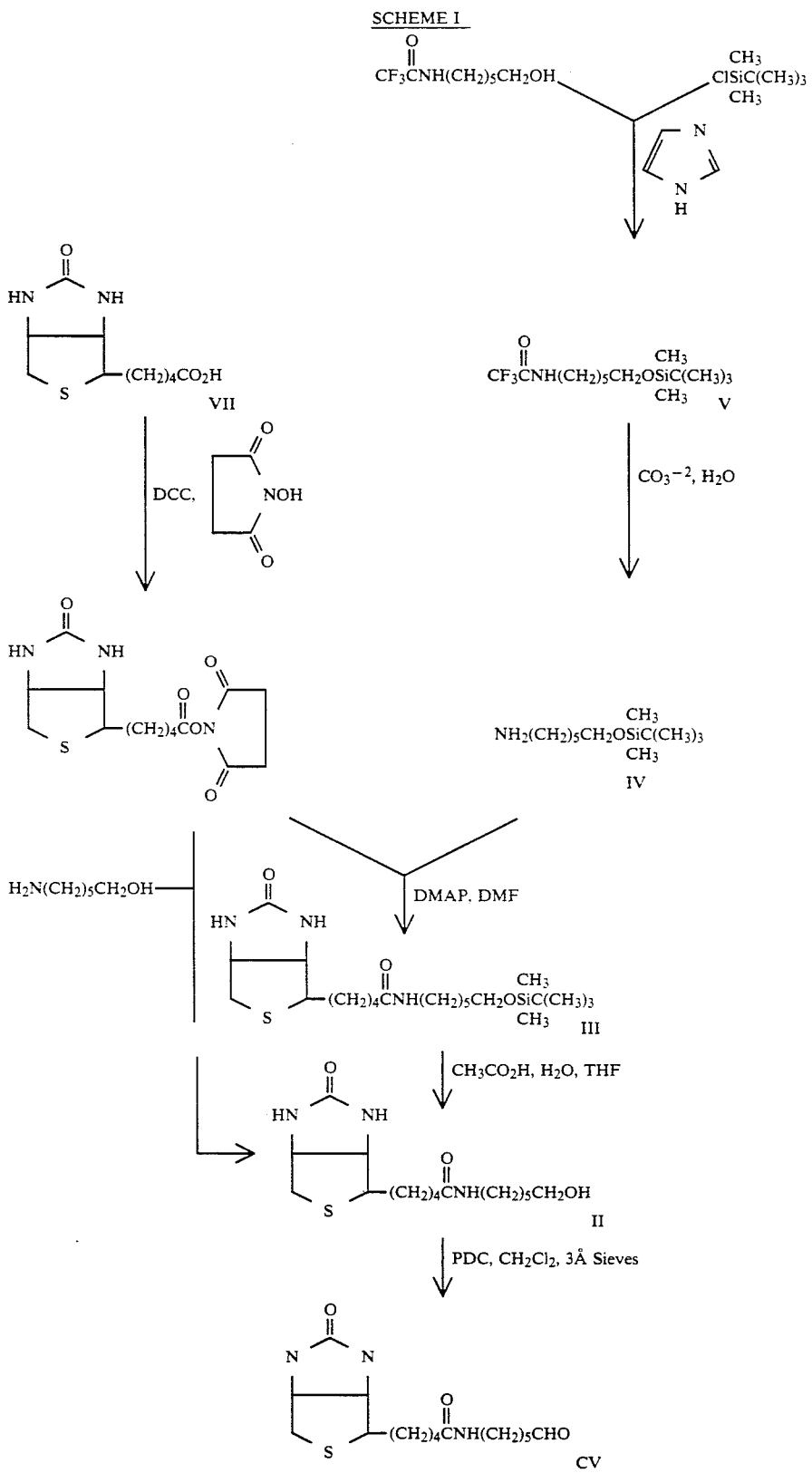

Compound V (6-tertbutyldimethylsilyloxy-1-hexyl-trifluoracetamide) was synthesized as follows:

To 1.00 g (4.8 mmoles) 6-trifluoracetamido-1-hexanol and 0.41 g (6.0 mmoles) imidazole in 12.5 ml of dry dimethylformamide (DMF) was added 0.91 g (6.0 mmole) tertbutyldimethylsilylchloride at 23° C. The solution was allowed to stir for three hours. The solvent was removed and the sample dried under high vacuum.

The solid was then extracted with 20% (v/v) ethylacetate in hexane. The organic layer was dried over anhydrous magnesium sulfate and concentrated to a colorless oil, yielding 1.40 g (89.6%) of Compound V.

The compound of Formula IV (6-tertbutyldimethylsilyloxy-1-hexylamine) was synthesized as follows:

To 1.10 g (3.4 mmole) of compound of Formula V was added 18 mls of a solution of 75% (v/v) methanol in water followed by 0.70 g (5 mmoles) of potassium carbonate. The solution was allowed to stir for 15 hours at 23° C. The solvent was removed and the solid was extracted with a mixture of 20% (v/v) ethylacetate in hexane. The organic layer was dried over anhydrous magnesium sulfate and concentrated to yield 0.72 g (91%) of a pale, yellow oil (Compound IV).

The compound of Formula VI (N-hydroxysuccinimidobiotin) was synthesized as follows according to the method of Becker et al. (Proc. Natl. Acad. Sci. U.S.A. 68, 2604(1971)):

Biotin (compound of Formula VII), in the D(+) configuration, was used as obtained from Sigma Chemical Company, Inc., St. Louis, Mo., U.S.A. (catalog no. B4501). 240 mg (1.0 mmole) biotin was dissolved in 5 ml of dry DMF. 210 mg (1.0 mmole) of dicyclohexylcarbodiimide (used as purchased from Aldrich Chemical Co., Milwaukee, Wis., U.S.A.) and 120 mg (1.2 mmole) of N-hydroxysuccinimide were added to the biotin solution and the resulting solution was stirred at 23° C. for 15 hours. The precipitate that formed was separated by filtration. The filtrate was then evaporated under reduced pressure and the resulting residue was washed twice with ethanol and finally recrystallized from hot acetonitrile to yield 230 mg (64%) of a white crystalline product (compound VI) having a melting point of 216°–218° C.

The compound of Formula III was synthesized as follows:

To 100 mg (0.3 mmole) of N-hydroxysuccinimidobiotin (Compound of Formula VI) was added 37 mg of N,N-dimethylaminopyridine and 104 mg of 6-tertbutyldimethylsilyloxy-1-hexylamine (Compound of Formula IV) in 10 ml of dry DMF. The solution was stirred for 16 hours at 23° C. The solution was then concentrated and the product isolated by flash chromatography using 20% (v/v) methanol in chloroform. 126 mg (94%) of 1-tertbutyldimethylsilyloxy-6-biotinyl-hexylamide (Compound of Formula III) was isolated as a white solid. The infrared spectrum of the compound of Formula III (in KBr) includes peaks at 1642 and 1704 cm$^1$. The proton nmr spectrum of the compound of Formula III in DMSO-$d_6$ has peaks at (shifts in ppm) 0.02 (singlet, 6H), 0.86 (singlet, 9H), 2.99 (multiplet, 1H), 3.55 (triplet, 2H), 4.12 (multiplet, 1H), 4.29 (multiplet, 1H), 6.35 (singlet, 1H) and 6.41 (singlet, 1H).

All references in the present specification to "flash chromatography" are to the method described by Still et al., J. Org. Chem. 43, 2923–2925(1978).

The Compound of Formula II (6-biotinylamide-hexan-1-ol) was prepared as follows:

Following the procedure of Nakai et al. (Chem. Lett. 1979, 1499), to remove the silyl protecting group, 126 mg (0.29 mmole) of the silyl ether (Compound of Formula III) was treated with a mixture of acetic acid/water/tetrahydrofuran (3:1:1, v/v) for 24 hours at 23° C. to yield the alcohol. 57 mg (60%) of Compound of Formula II was thereby isolated.

An alternative procedure used to prepare the compound of Formula II is as follows:

To 0.5 g (1.5 mmoles) of Compound VI in 5 ml of DMF was added 0.15 g (1.3 mmoles) of 6-amino-1-hexanol and the reaction mixture was stirred for 3 hours at 23° C. After concentration under reduced pressure, and flash chromatography using 20% (v/v) methanol in chloroform, II was obtained in 94% yield, identical in NMR and IR to the product of the acid hydrolysis of III.

Finally, the biotin-linker aldehyde of Formula CV (6-biotinylamide-hexan-1-al) was prepared as follows:

To 10 mg (30 micromole) of the alcohol of Formula II was added 28 mg (75 micromole) of pyridinium dichromate and 50 mg of 3 Angstrom molecular sieves in 10 ml of methylene chloride. After stirring for 3 hours at 23° C., 30 ml of diethyl ether was added to the reaction mixture, which was then filtered through a plug of silica gel 60 (Merck grade, obtained from Aldrich Chemical Co., Milwaukee, Wis., U.S.A.). The eluant was dried and purified by flash chromatography using 10% (v/v) methanol in chloroform. 3 mg (30%) of biotin linker aldehyde of Formula CV was obtained.

(B) Synthesis through Acid and Acyl Chloride Intermediates

The method of synthesizing biotin-linker aldehyde through acid and acyl chloride intermediates is illustrated in Scheme II.

SCHEME II

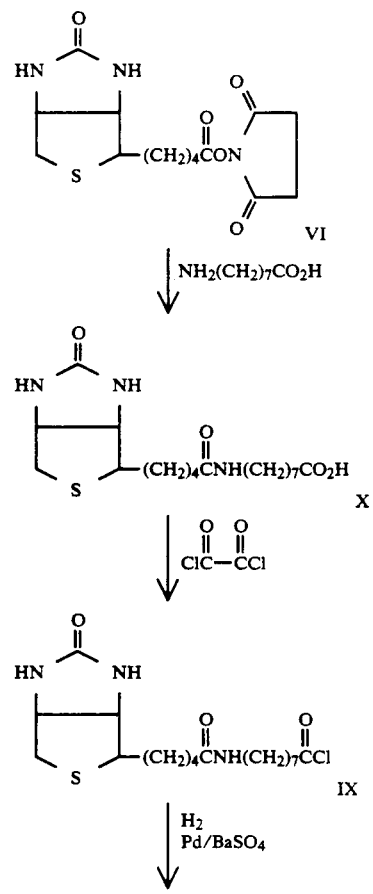

-continued
SCHEME II

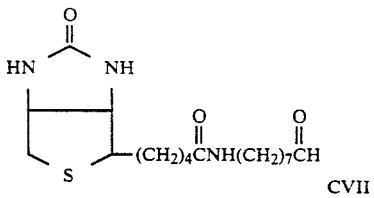

CVII

To 250 mg (0.73 mmoles) of N-hydroxysuccinimide biotin (Formula VI) was added 0.116 g (0.73 mmoles) of 8-amino octanoic acid in 5 ml of DMF and 0.8 ml of 0.1 M sodium bicarbonate buffer, pH 8.5. The mixture was warmed to 55° C.–60° C. and allowed to cool to 23° C. After stirring at 23° C. for 14 hours, the solvent was removed under reduced pressure and the solid crystallized from acetonitrile to give 0.264 g (93%) of 8-biotinylamide-1-octanoic acid (Formula X).

8-biotinylamide-1-octanoic acid was converted to the acid chloride (Formula IX) by treatment with oxalyl chloride. To 100 mg (0.26 mmoles) of Compound X was added 0.125 ml (1.44 mmoles) of oxalyl chloride in 6 ml of benzene containing 2 drops of DMF. After 30 minutes at 23° C., the reaction mixture was dried in vacuo. The acid chloride was directly converted to the aldehyde by adding 20 ml of freshly distilled tetrahydrofuran and 175 mg of 5% palladium on barium sulfate; hydrogen gas was bubbled through the mixture for 12 hours. The analysis of the reaction mixture by TLC (thin-layer chromatography) showed several spots, one of which (Compound of Formula VII) sprayed positive for aldehydes with 2,4-dinitrophenyl hydrazine.

(C) Synthesis of Linker-Aldehyde from Biotin Hydrazide

Another method to make a biotin-linker aldehyde compound is illustrated in Scheme III.

SCHEME III

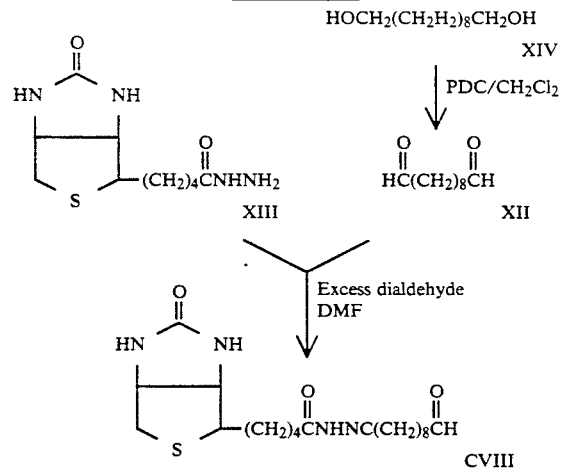

1,10-decane dialdehyde was prepared from the 1,10-decane diol of Formula XIV as follows:

436 mg (2.5 mmoles) of the 1,10-decanediol was added to 2.26 g (6 mmoles) pyridinium dichromate and 2.5 g of 3 Angstrom molecular sieves in 25 ml methylene chloride. After 2 hours of stirring at 23° C., TLC analysis of the mixture showed complete conversion of the diol to the dialdehyde. The reaction mixture was poured into 100 ml of diethyl ether and this in turn was passed through a plug of silica gel 60. The plug was then further washed with 50 ml methylene chloride and the organic layers were combined and then concentrated under reduced pressure to a white solid. The dialdehyde was then purified by chromatography on silica gel 60 using chloroform as an eluant. 250 mg (58%) of dialdehyde was isolated as a clear oil.

Biotin-linker aldehyde of Formula CVIII was then prepared from biotin-hydrazide (Formula XIII) and the 1,10-decane dialdehyde of Formula XII as follows:

To 70 mg (0.27 mmoles) of biotin-hydrazide (Calbiochem-Behring, Inc., San Diego, Calif., U.S.A.) was added 175 mg (1 mmole) of the 1, 10-decane dialdehyde in 5 ml of 20 parts DMF in 1 part $H_2O$ (by volume). After stirring for 1 at 23° C., analysis of the reaction mixture by thin layer chromatography showed the appearance of product (Compound of Formula CVIII). Silica gel chromatography using 10% (v/v) methanol in chloroform allowed clean separation of the dialdehyde and the biotin linker aldehyde. The peak fraction from the chromatograph was pooled and dried to yield 80 mg (72%) of the solid biotin aldehyde (Compound of Formula CVIII). The infrared spectrum of the compound of Formula CVIII (in KBr) included peaks at 1664 and 1703 $cm^1$.

When glutaraldehyde was used in place of 1, 10-decane dialdehyde in the foregoing procedure, similar results were obtained, with the product compound having 3 rather than 8 carbon atoms in the alkyl chain linked to the aldehyde group.

(D) Synthesis of Linker-Aldehyde through Biotin-Linker Acetals

Scheme IV illustrates the synthesis of biotin-linker aldehyde through biotin-linker acetal.

The Compound of Formula XVI (6-ethylenedioxy-1-hexylamine) was prepared in three steps from 6-amino-1-hexanol as follows:

To 4 gm (34 mmole) of 6-amino-1-hexanol in 20 ml of 0.05 M sodium bicarbonate, pH 10, was added 5.8 ml (45 mmole) of S-ethyltrifluorothioacetate with stirring at 23° C. The pH was maintained between 9.5 and 10 with 1 M NaOH; and, after three hours, the aqueous solution was extracted five times, each with 50 ml of chloroform. The chloroform solution was dried over anhydrous magnesium sulfate and concentrated under reduced pressure. Recrystallization from chloroform afforded 5.6 gms (79%) of product (6-trifluroacetamido-1-hexanol).

To 2.1 gm (10.1 mmole) of the 6-trifluroacetamido-1-hexanol in 40 ml of methylene chloride was added 3 gm (10.64 mmole) of pyridinium dichromate and 4.4 gm of 3 Angstrom molecular sieves, and the reaction was allowed to proceed with stirring for 3 hours at 23° C. After addition of 250 ml of ethyl acetate, the reaction mixture was filtered through a small bed of silica gel 60 and concentrated in vacuo. Flash chromatography using 50% (v/v) ethyl acetate in hexane afforded 1.48 gms (70%) of 6-trifluroacetamido-1-hexanal.

SCHEME IV

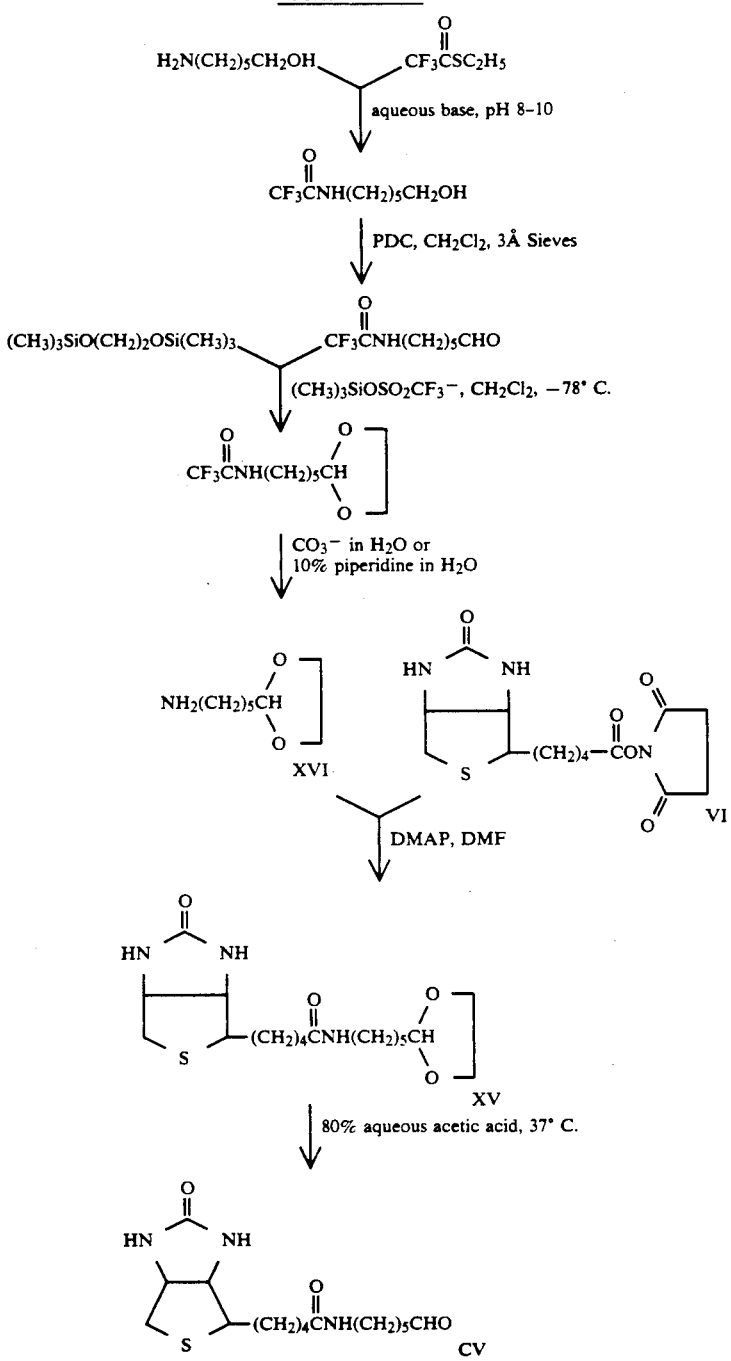

To 1.4 gms (6.8 mmole) of 6-trifluroacetamido-1-hexanal in 21 ml of methylene chloride under nitrogen at −78° C. was added 1.8 ml (7.48 mmole) of 1,2-bis(trimethylsilyloxy)ethane and 0.14 ml (0.73 mmole) of trimethylsilyltrifluoromethane sulfonate, and the solution was stirred for three hours at −78° C., followed by another 0.5 hours at 23° C. The reaction mixture was taken up in 100 ml methylene chloride, which was then washed with 30 ml of saturated sodium bicarbonate solution. The aqueous layer was extracted with 50 ml of methylene chloride; and the organic layers were combined, dried over anhydrous magnesium sulfate, concentrated, and flash chromatographed with 50% (v/v) ethyl acetate in hexane to give 1.3 gms (77%) of the product, 6-ethylenedioxy-1-hexyltrifluorocetamide.

To 0.380 gm (1.49 mmole) of 6-ethylenedioxy-1-hexyltrifluoracetamide in 7.5 ml of 20% (v/v) water in methanol was added 0.3 gm (2.2 mmole) of potassium carbonate, and the reaction mixture was stirred for 14 hours at 23° C. After concentrating the reaction mixture, it was taken up in 15 ml of brine (saturated aqueous NaCl) and extracted three times, each with 50 ml of diethyl ether, and also four times, each with 50 ml of chloroform. The organic layers were dried, combined and concentrated under reduced pressure to give an oil weighing 0.19 gms (80%) which gave a positive color with ninhydrin on a silica gel plate developed in a mixture of butanol/acetic acid/water (4:1:1). This oil, which consists essentially of the compound of Formula XVI, was used directly for synthesizing the biotin-linker acetal of Formula XV.

Alternately, the same conversion was carried out in quantitative yield by treating 6-ethylenedioxy-1-trifluoracetamide with 10% piperidine in water for 45 minutes at 23° C. Lyophilization of the reaction mixture resulted in complete recovery of the desired compound.

The compound of Formula XV was prepared from the compound of Formula XVI and N-hydroxysuccinimido-biotin (compound of Formula VI, prepared as described in Example VA) as follows:

To 0.090 gm (0.26 mmole) of N-hydroxysuccinimido-biotin in 4 ml of dry DMF were added 0.032 gm (0.26 mmole) of N, N-dimethylamino-pyridine and 0.05 gm (0.31 mmole) of the 6-ethylenedioxy-1-hexylamine oil (Compound XVI) and the mixture was stirred for 14 hours at 23° C. Concentration of the solution under reduced pressure, followed by medium pressure liquid chromatography on a Lobar pre-packed Si 60 column (from Merck, Darmstadt, West Germany or EM Industries, Inc., Cherry Hill, N.J., U.S.A.), provided 0.05 gm (50%) of the desired product of Formula XV (biotinyl (N-6-ethylenedioxyhexyl)amide). The following data have been obtained for the compound of Formula XV: Molecular weight (high resolution mass spectrum): calcd. 385.2035, found 385.2039. Elemental analysis: calcd. C(56.08), H(8.10), N(10.90); found C(55.78), H(8.09); N(10.72). Proton nmr in DMSO-$d_6$ (shifts in ppm): 2.04 (triplet, 2H), 3.71–3.89 (multiplet, 4H), 4.13 (multiplet, 1H), 4.30 (multiplet, 1H), 4.30 (multiplet, 1H), 4.74 (triplet, 1H), 6.35 (singlet, 1H), 6.42 (singlet, 1H), 7.73 (triplet, 1H).

Conversion of compound XV to the aldehyde (CV) was effected in quantitative yield on treatment with 80% aqueous acetic acid at 37° C. for 3 hours, followed by lyophilization.

Alternatively, other acetal groups, in place of that of the compound of Formula XVI, can be employed as protecting groups in preparing the aldehyde. Such alternative acetal protecting groups are known in the art (see T. Greene (1981), "Protective Groups in Organic Synthesis", Chapter 4; Wiley and Sons, N.Y.). Illustrative is a compound of Formula XVIA:

EXAMPLE VI

PABSAT In this Example, preparation of PABSAT is described. The preparation is illustrated in Scheme V.

To prepare a halophenyl or nitrophenyl analog of PABSAT, the corresponding halophenyl or nitrophenyl analog of p-acetamido-benzene sulfonylchloride (compound of Formula XIX) is used in the preparative procedure.

To a solution of 0.2 gm (1.1 mmoles) of aminothiadiazole (XX) in 4 ml of dry pyridine at 0° C. was added, dropwise, a solution of 0.28 gm (1.12 mmoles) of p-acetamido-benzenesulfonyl chloride in 3 ml of dry pyridine. The reaction mixture was subsequently warmed to 23° C., and magnetically stirred for 16 hours. After concentration under reduced pressure, the crude product was dissolved in methanol, and treated with activated charcoal, filtered, concentrated under reduced pressure, and purified by flash chromatography using methylene chloride-methanol (65:25) to give 0.31 gm of the benzolamide derivative (Compound XVIII) in 75% yield.

To 0.14 gm (0.37 mmole) of Compound XVIII was added 3.5 ml of 1N HCl, and the reaction mixture was refluxed for three hours. On cooling, the solution was neutralized with ammonium hydroxide, and concentrated under reduced pressure to give a white solid in quantitative yield, which was pure PABSAT (compound of Formula XVII).

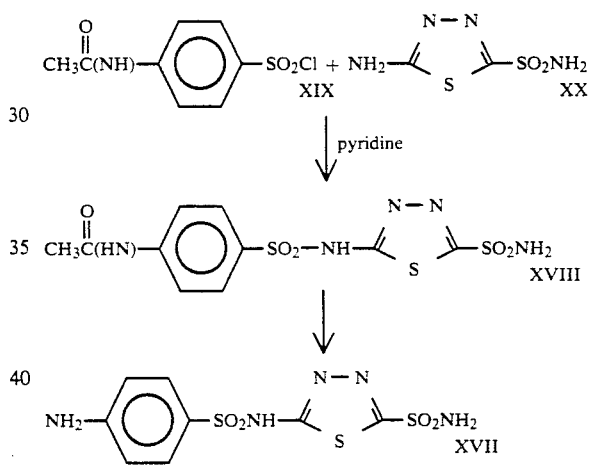

EXAMPLE VII

PABSAT - Linker Aldehyde

In this Example, methods are described for preparing linker-aldehyde compounds which are suitable for linking PABSAT (and halophenyl and nitrophenyl analogs thereof) to polynucleotides with $N^4$-aminocytosine moieties and thereby preparing probes of the invention.

The methods of this Example are illustrated in Schemes VIA and VIB.

The methods can also be employed in preparing linker-aldehydes of aminothiaizole or sulfanilamide for linking those compounds to $N^4$-amino-cytosine-containing polynucleotides to make probes of the invention. This is accomplished by replacing PABSAT with aminothiadiazole or sulfanilamide in the reaction with the acetal acetyl chloride of Formula XXIII in Scheme VIB and preparing the aminothiadiazole or sulfanilamide linker-aldehyde from the resulting aminothiadiazole or sulfanilamide analog, respectively, of the acetal of Formula XXII.

SCHEME VIA
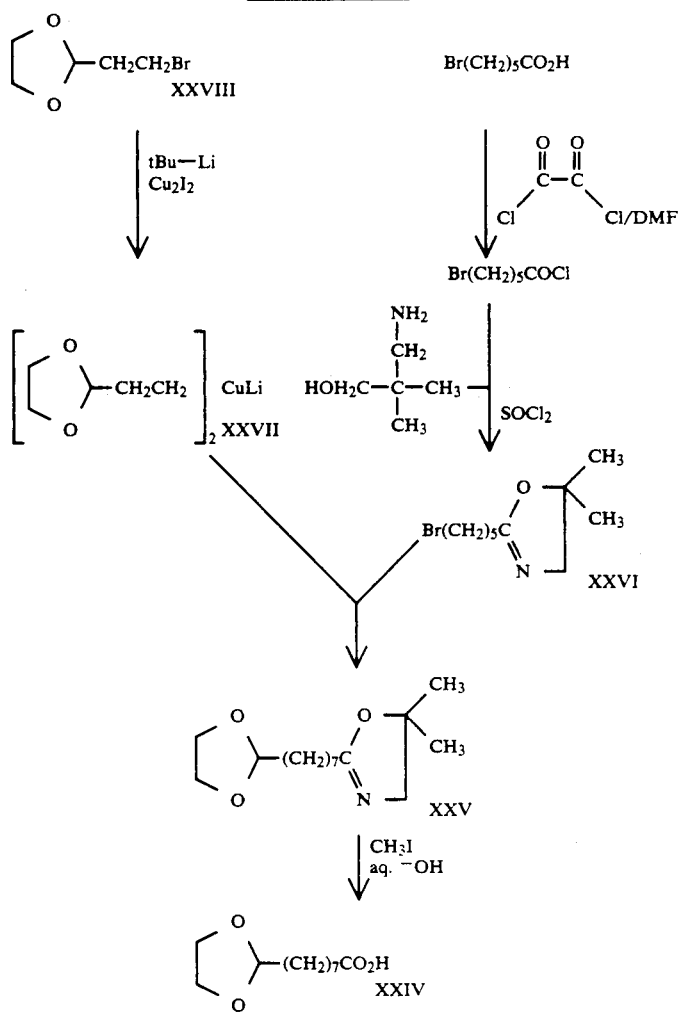
SCHEME VIB
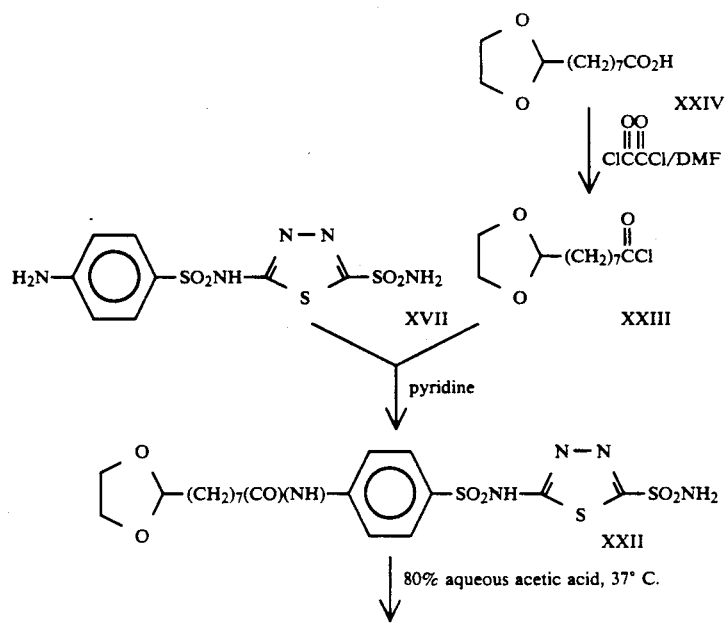

SCHEME VIB

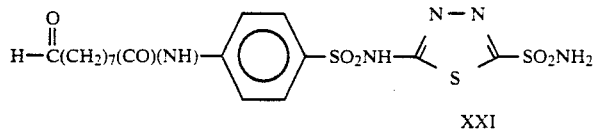

XXI

To 1.1 gm (5.7 mmole) of bromohexanoic acid in 15 ml of dry benezene was added 2 ml (23 mmole) of oxalyl chloride and 2 drops of DMF at 23° C. After evolution of gas from the reaction ceased after 10 minutes, the solution was concentrated in vacuo, and the crude chloride was taken up in 5 ml of dry $CH_2Cl_2$. To this solution was added a solution of 0.55 gm (6 mmole) of 2-methyl-2-aminomethyl-1-propanol in 2 ml of $CH_2Cl_2$ under nitrogen at 0° C. and the mixture was stirred for 15 minutes, and then warmed to 23° C. After concentration in vacuo, excess thionyl chloride was then added and after 30 minutes the reaction mixture was concentrated under reduced pressure. The crude product was purified by flash chromatography using 50% ethyl acetate in hexane to afford 0.75 gm (53%) of very pure oxazoline of Formula XXVI.

To 0.220 gm (1.2 mmole) of 2-(2-bromoethyl)-1,3-dioxolane (compound of Formula XXVIII) in 1 ml of tetrahydrofuran at −78° C. under nitrogen, was added 1.4 ml (2.4 mmole) of 1.7 M solution of tert-butyl lithimm in pentane, and the yellow solution was stirred for 15 minutes. This solution was transferred via a double-tipped needle under nitrogen into a flask containing 0.12 gm of cuprous iodide (0.6 mmole) and the reaction mixture was stirred for 30 minutes at −78° C. To the cuprate, compound of Formula XXVII, was added a solution of 0.05 gm (0.2 mmole) of the bromo-oxazole of Formula XXVI in 1 ml of tetrahydrofuran, and the reaction was allowed to proceed at −50° C. for 5 hours, followed by warming to 23° C. and stirring for 2 hours. Concentration of the reaction mixture in vacuo, followed by solution in methanol and filtration through a silica gel-60 plug, afforded the crude product. This was purified by flash chromatography using 20% ethyl acetate in hexane to give 0.03 gm (56%) of pure oxazoline-acetal of Formula XXV as a clear oil.

To 0.040 gm (0.15 mmole) of the acetal-oxazoline for Formula XXV is added 0.5 ml of methyl iodide and the mixture is stirred for 16 hours at 23° C. After concentration under a stream of nitrogen, 1 ml of a 1N sodium hydroxide solution is added, and the mixture is stirred for 15 hours at 23° C. After neutralization with 10% hydrochloric acid, followed by extraction with ether, and concentration under vacuum, the desired acetal-acid of Formula XXIV is obtained.

To 0.030 gm (0.14 mmole) of the acetal-acid of Formula XXIV in 2 ml of dry benzene is added 0.05 ml (0.56 mmole) of oxalyl chloride and one drop of DMF. The solution is stirred for 10 minutes and concentrated under vacuum. The resulting oil (acylchloride of Formula XXIII) is then taken up in 1 ml of pyridine, and 0.045 gm (0.14 mmole) of PABSAT (Formula XVII) is introduced as a solution in 1 ml of pyridine. The mixture is stirred for 5 hours, and then concentrated in vacuo. Flash chromatography of the crude using 30% methanol in chloroform affords the acetal-linker-benzolamide derivative of Formula XXII.

The compound of Formula XXII is converted to the desired PABSAT linker aldehyde of Formula XXI by treatment with 80% aqueous acetic acid for 3 hours at 37° C. followed by lyophilization.

EXAMPLE VIII

Fluorescein-Linker Aldehyde

A mixture of 10.8 mg (0.28 mmoles) of fluorescein isothiocyanate and 23 mg (0.14 mmoles) of 6-ethylenedioxy-1-hexylamine in 1.5 ml of dry pyridine was stirred at 23° C. for one hour. After concentrating the solution under reduced pressure, the crude product was purified by flash chromatography using 10% methanol in methylene chloride to afford 11 mg (72%) of fluorescein-linker acetal. This was quantitatively converted to the aldehyde by treatment with 80% aqueous acetic acid at 37° C. for 3 hours followed by lyophilization.

The procedure of the previous paragraph can be carried out with other isothiocyanate-derivatized fluorescent moieties, such as tetramethylrhodamine isothiocyanate and tetraethylrhodamine isothiocyanate, to prepare other fluorescent tag moiety-linker aldehydes.

The procedure can be carried out also with the isocyanate derivatives of the fluorescent moieties in place of the isothiocyanate derivatives. The isocyanate derivatives, like the isothiocyanate, are known.

EXAMPLE IX

Probes with Biotinyl, Iminobiotinyl or Sulfenylbiotinyl as Tag Moiety

To prepare a probe of the invention with biotinyl, iminobiotinyl, or sulfenylbiotinyl as tag moiety, using a linker aldehyde compound prepared in accordance with Example V, the following procedure is employed:

100 micrograms of a polynucleotide with the sequence of the probe is treated as described in Example III to transaminate (convert to $N^4$-aminocytosine) about 10% to about 50% of the cytosines in the polynucleotide. The reaction is stopped by passing the solution through a Sephadex G-25 spin column and isolating the modified polynucleotide by collecting the effluent. To the effluent (containing approximately 75 microgram (ug) of polynucleotide in approximately 150 microliters (ul)) is added 40 ul of linker compound solution (5 mg/ml in DMSO). After 30 minutes at 37° C., the mixture is passed through a Sephadex G-25 spin column and tagged polynucleotide is obtained in the collected effluent.

Concentration of the tagged probe is quantitated by UV absorbance at 260 nm and biotinylation is confirmed by spotting 1 ul of the probe solution on nitrocellulose paper and detecting the probe as described by Leary et al. (1983), supra., using avidin-DH and biotinylated alkaline phosphatase polymer.

EXAMPLE X

Probes With PABSAT, Aminothiadiazole or Sulfanilamide as Tag Moiety

To prepare probe of the invention with PABSAT, aminothiadiazole or sulfanilamide as tag, the following procedure is employed:

First, following the procedure of Example III, a polynucleotide with the sequence of the probe is modified to convert about 10 to about 50% of its cytosines into $N^4$-aminocytosines. The modified polynucleotide (approximately 75 ug in approximately 150 ul) is then mixed with 50 ul (5 mg/ml in DMSO) of a solution of sulfonamide linker aldehyde (e.g., compound of Formula XXI) prepared in accordance with Example VII. After 30 minutes at 37° C., unreacted aldehyde is separated from labeled probe by spin column chromatography, as in Example IX.

Concentration of tagged probe is determined by UV absorbance at 260 nm. Attachment of tag is confirmed by detecting carbonic anhydrase polymer reporter group bound to tag, following procedures in Example XIII.

EXAMPLE XI

Probes with Fluorescein or Tetramethylrhodamine As Tag Moiety

To prepare probe of the invention with fluorescein or tetramethylrhodamine as tag moiety, the following procedure is employed:

First, following the procedure of Example III, a polynucleotide with the sequence of the probe is modified to convert between about 10% to about 50% of its cytosines into $N^4$-aminocytosines. The modified polynucleotide (approximately 75 ug in approximately 150 ul) is then mixed with 50 ul of a solution (5 mg/ml in DMSO) of a fluorescein-linker aldehyde or tetramethylrhodamine-linker aldehyde prepared in accordance with Example VIII. After 30 minutes at 37° C., unreacted aldehyde is separated from labeled probe by spin column chromatography, as in Example IX.

Concentration of tagged probe is determined spectroscopically. Attachment of fluorescent tag is confirmed by fluorescence emission spectroscopy.

EXAMPLE XII

Use of Probes of the Invention in Nucleic Acid Hybridization Assay

The competency of probes of the invention in hybridization assays was established in a Southern hybridization protocol.

Polynucleotide B (Example I) was transaminated according to Example III in a reaction lasting 10 minutes, so that, on the average, between 1 and 2 cytosines per molecule of polynucleotide were converted to $N^4$-aminocytosine. The $N^4$-aminocytosine-containing polynucleotide was then biotinylated according to Example IX with the linker aldehyde of Formula CV. The biotinylated polynucleotide B was used in the Southern protocol.

A 730 base pair HindIII-SalI DNA fragment, which is a portion of the coding segment of the alcohol oxidase gene, was isolated from Pichia pastoris by standard procedure. See Ellis et al., Mol. Cell. Biol. 5, 1111–1121(1985). By standard procedures, this fragment was cloned in both M13mp18 and M13mp19 in E. Coli JM103. The M13mp18 clones produce phage with DNA with a segment identical in sequence to Polynucleotide B. The M13mp19 clones produce phage with DNA with a segment with a sequence complementary to that of Polynucleotide B.

Large quantities of each type of phage were prepared by standard methods with E. coli JM103. After purification, DNAs from the M13mp18 and M13mp19 phage were attached to separate nitrocellulose filters by means of Manifold II Slot Blotter apparatus (Schleicher and Schuell, Inc., Keene, N.H., U.S.A.). As a positive control, a denatured, double-stranded E. coli plasmid, pUC19, was also attached to a filter by the same method. On each filter, the DNA was aliquoted in bands of 500 ng, 100 ng, 10 ng, 1 ng, 100 pg, 10 pg, and 1 pg.

Attachment was followed by baking in a vacuum oven at 80° C. The filters were then prehybridized for 2 hours at 42° C. with 6 x SSPE, 0.5% (w/v) sodium dodecyl sulfate (SDS), 1x Denhardt's solution, 1 mg/ml herring sperm DNA. Following the prehybridization, the filters were hybridized with probe as follows:

| | |
|---|---|
| Filter 1: (M13mp19 DNA) | probed with 1 μg of biotinylated Polynucleotide B, at 300 ng/ml in hybridization solution. |
| Filter 2: (M13mp18 DNA) | probed with 1 μg of biotinylated Polynucleotide B, at 300 ng/ml in hybridization solution. |
| Filter 3: (pUC19 DNA) | probed with 300 ng pUC19 DNA nick-translated with a biotinylated 2'-deoxyuridine-5'-triphosphate, essential according to the procedure of Langer et al., Proc. Natl. Acad. Sci.(U.S.A.) 78, 6633–6637(1981) (using a nick-translation kit purchased from Bethesda Research Laboratories, Gaithersburg, Maryland, U.S.A.) and at 100 ng/ml in hybridization solution. |

Hybridizations were done at 42° C. for 15 hours. Hybridization solution was 6 x SSPE, 0.5% (w/v) SDS, and 1x Denhardt's solution. After the hybridization, the filters were washed as follows:

| | |
|---|---|
| Filter 1: | 2 × SSC for 15 minutes, twice, at room temperature |
| | 2 × SSC for 15 minutes, once, at room temperature |
| Filter 2: | Same as filter 1 |
| Filter 3: | 2 × SSC and 0.1% (w/v) SDS for 15 minutes, twice, at room temperature |
| | 2 × SSC and 0.1% (w/v) SDS for 15 minutes, twice, at 42° C. |
| | 2 × SSC for 15 minutes, once, at room temperature |

Definitions of SSC, SSPE, and Denhardt's Solution are known in the nucleic acid hybridization art. See Maniatis et al., Molecular Cloning: A Laboratory Manual, Cold Spring Harbor Laboratory Press, Cold Spring Harbor, N.Y., U.S.A.(1982).

The filters were then developed with streptavidin-biotinylated alkaline phosphatase polymer as reporter group, prepared according to the procedure of Leary et al. (1983), supra, using substrate of alkaline phosphatase with associated dye for colorimetric indication, also according to the procedure of Leary et al.(1983), supra.

Color development was monitored after 1.5 hours.

The test filter (Filter 1) showed hybridization down to the band with 100 pg DNA. The negative control filter (Filter 2) showed no hybridization. The positive control filter (Filter 3) showed hybridization down to the band with 1 pg DNA.

EXAMPLE XIII

Use of Aminothiadiazole-Benzolamide Derivatized Probes in Hybridization Assays In this Example, use of probes tagged with aminothiadiazole-benzolamide derivatives, such as PABSAT, is described.

Following the procedure of Example IV, Polynucleotide C. is synthesized to have $N^4$-aminocytosines at positions 6, 20, 28, and 34 (from the 5'-end).

Following the procedure of Example X, using PABSAT linker aldehyde of Formula XXII prepared as described in Example VII, the $N^4$-aminocytosine-containing Polynucleotide C. is converted to probe with PABSAT linked to the $N^4$-amino nitrogens of the modified cytosines.

DNA is isolated from two mammalian cell cultures, one known to be infected with Epstein-Barr virus (EBV) and the other known to be EBV-free. Approximately 5 ug of protein-free DNA from each culture is affixed to a separate, prewetted nitrocellulose filter using standard blotting techniques.

The filters are then prehybridized as described in Example XII.

Each filter is then hybridized with 1 ug of PABSAT-derivatized polynucleotide C, as described in Example XII, at 300 ng/ml in hybridization solution.

Following the hybridization, the filters are washed, also as in Example XII.

The filters are then developed with a reporter system based on the fluorescein-diacetate assay of Leary et al.(1978), supra, for bovine erythrocyte carbonic anhydrase B as follows:

Bovine erythrocyte carbonic anhydrase B is purchased from Sigma Chemical Co., St. Louis, Mo., U.S.A. and purified as described by Armstrong et al., J. Biol. Chem. 244, 5137-5149(1966). The purified protein is polymerized by the procedure of Epton, supra.

The filters with hybridized probe are incubated for 5 minutes at room temperature with a solution of protein polymer (20 ug/ml) in Tris buffer (pH 7.6). After the incubation, the filters are washed 5 times with 0.05M potassium phosphate buffer, pH 6.8, to remove protein polymer that has not bound to probe through PABSAT tag.

Finally, the filters are incubated for 4 hours at room temperature with a solution of 1 mM fluorescein diacetate in 0.05 M potassium phosphate buffer, pH 6.8.

After the incubation with fluorescein diacetate, the filter with EBV DNA exhibits a fluorescent yellow-green color while the other filter exhibits no fluorescence.

While the foregoing examples illustrate the present invention, they are not intented to limit the scope thereof. The skilled in the art will recognize, from the exemplified embodiments, modifications and variations that are within the spirit and scope of the invention described and claimed herein.

What is claimed is:

1. A compound of the formula

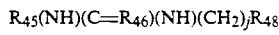

$$R_{45}(NH)(C=R_{46})(NH)(CH_2)_jR_{48}$$

wherein $R_{45}$ is fluorescein, tetramethylrhodamine or tetraethylrhodamine; $R_{46}$ is oxygen or sulfur; $R_{48}$ is

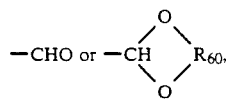

wherein $R_{60}$ is alkylene of 2 or 3 carbon atoms; and wherein j is 2 to 20.

2. A compound according to claim 1 wherein j is 5 to 8.

3. A compound according to claim 2 wherein $R_{46}$ is sulfur.

UNITED STATES PATENT AND TRADEMARK OFFICE
CERTIFICATE OF CORRECTION

PATENT NO. : 5,130,446                          Page 1 of 2
DATED       : July 14, 1992
INVENTOR(S) : Musso et al.

It is certified that error appears in the above-identified patent and that said Letters Patent is hereby corrected as shown below:

On the title page, Item [75]:

At Inventors, after "Gary F. Musso; Soumitra Ghosh, both of San Diego" insert --, Calif.--,
and delete "; Leslie E. Orgel, La Jolla; Geoffrey M. Wahl, San Diego, all of Calif.; Emil T. Kaiser, New York, N.Y.".

At Column 7, line 31, in Formula XXXII change "$(CH_2)_K$" to --$(CH_2)_k$--.

At Column 8, line 13, change "where" to --wherein--.
At Column 8, line 48 and 68 (both occurrences) and at Column 9, line 1, change "0" to --O--.
At Column 12, line 20, change "$R_3=C=N-R_6$" to --$R_3=C=N-R_5-R_6$--.
At Column 15, line 33, change "spectroscope" to --spectroscopy--.
At Column 16, line 20, change "incuoation" to --incubation--.
At Column 17, under the Formula having the moiety "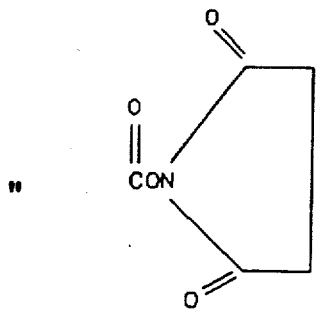"                    "       insert --VI--.

UNITED STATES PATENT AND TRADEMARK OFFICE
CERTIFICATE OF CORRECTION

PATENT NO. : 5,130,446

DATED : July 14, 1992

INVENTOR(S) : Musso et al.

It is certified that error appears in the above-identified patent and that said Letters Patent is hereby corrected as shown below:

At Column 21, line 45, in Formula XIV, change "$(CH_2H_2)$" to --$(CH_2)$--.

At Column 22, line 20, after "1" insert --hour--.

At Column 29, lines 29-30, change "lithimm" to --lithium--.

At Column 33, lines 23 and 28, change "C." to --C--.

Signed and Sealed this

First Day of March, 1994

Attest:

*Attesting Officer*

BRUCE LEHMAN

*Commissioner of Patents and Trademarks*